(12) United States Patent
Karsenti

(10) Patent No.: US 8,858,521 B2
(45) Date of Patent: Oct. 14, 2014

(54) DISPOSABLE DIAPER WITH INTEGRAL DISPOSAL SYSTEM

(76) Inventor: Samuel Karsenti, Jerusalem (IL)

(*) Notice: Subject to any disclaimer, the term of this patent is extended or adjusted under 35 U.S.C. 154(b) by 537 days.

(21) Appl. No.: 13/255,918

(22) PCT Filed: Mar. 10, 2010

(86) PCT No.: PCT/IL2010/000198
§ 371 (c)(1),
(2), (4) Date: Sep. 12, 2011

(87) PCT Pub. No.: WO2010/103516
PCT Pub. Date: Sep. 16, 2010

(65) Prior Publication Data
US 2012/0016332 A1    Jan. 19, 2012

(30) Foreign Application Priority Data
Mar. 12, 2009 (IL) .......................... 197570

(51) Int. Cl.
*A61F 13/15* (2006.01)
*A61F 13/551* (2006.01)

(52) U.S. Cl.
CPC .......... *A61F 13/5513* (2013.01); *A61F 13/551* (2013.01); *A61F 2013/55125* (2013.01); *A61F 2013/55155* (2013.01)
USPC ................................................. 604/385.02

(58) Field of Classification Search
CPC ............ A61F 13/5512; A61F 13/5515; A61F 2013/55125; A61F 2013/55155
USPC ............................. 604/385.13, 385.02, 385.06
See application file for complete search history.

(56) References Cited

U.S. PATENT DOCUMENTS

| | | | | |
|---|---|---|---|---|
| 4,430,087 A | * | 2/1984 | Azpiri ................... | 604/385.13 |
| 4,923,455 A | | 5/1990 | Dean et al. | |
| 4,968,312 A | * | 11/1990 | Khan .................... | 604/385.13 |
| 5,037,414 A | * | 8/1991 | Booth ................... | 604/385.13 |
| 5,836,931 A | * | 11/1998 | Toyoda et al. ......... | 604/385.29 |
| 2003/0009144 A1 | | 1/2003 | Tanzer et al. | |
| 2005/0256487 A1 | * | 11/2005 | Williams ............... | 604/385.19 |
| 2006/0058750 A1 | | 3/2006 | DiGirolamo et al. | |
| 2011/0306945 A1 | * | 12/2011 | Drevik et al. .......... | 604/385.13 |

FOREIGN PATENT DOCUMENTS

WO   WO 2008/023363   2/2008

* cited by examiner

*Primary Examiner* — Lynne Anderson
*Assistant Examiner* — Bradley Philips

(57) ABSTRACT

The present invention provides a diaper assembly comprising an integral disposal system, the diaper assembly comprising a disposable diaper comprising an outer layer comprising an aperture on an outer surface thereof, an inner layer and an absorbent layer disposed between said outer layer and said inner layer and a bag disposed between said outer layer and said inner layer, said bag being folded and adapted to be retrieved via the aperture and to receive and enclose said diaper, wherein the absorbent layer is of a greater thickness than the height of the folded bag.

19 Claims, 8 Drawing Sheets

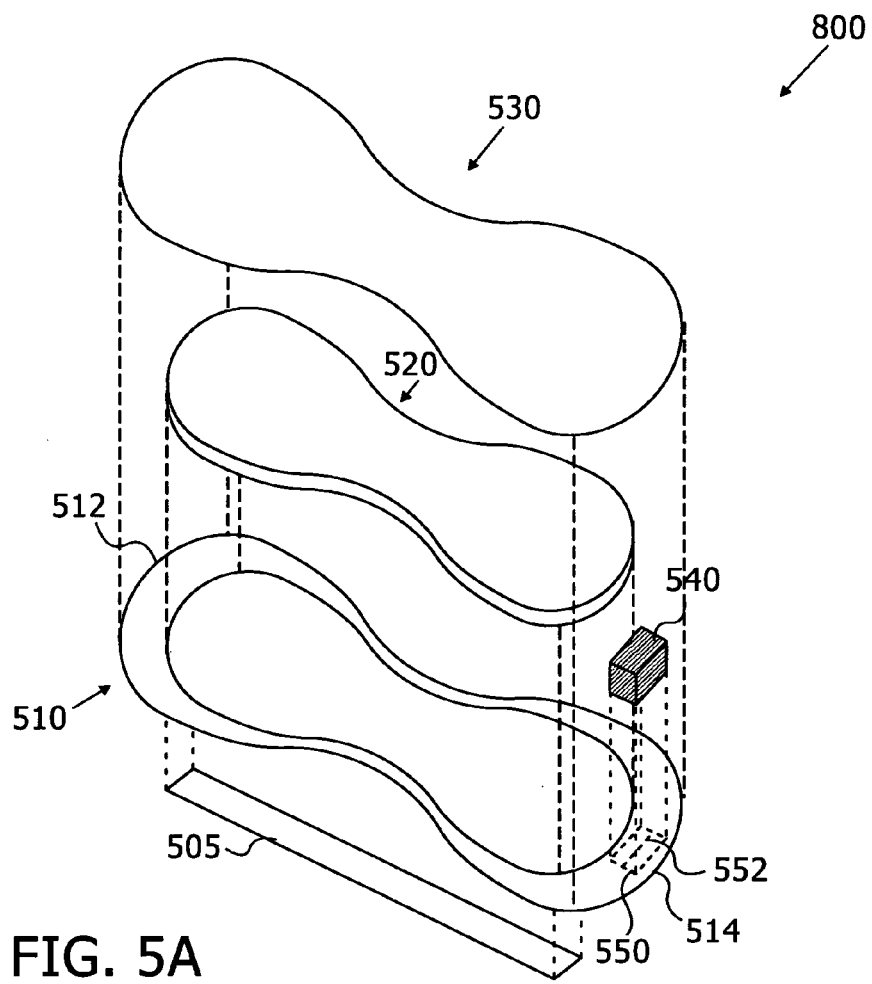
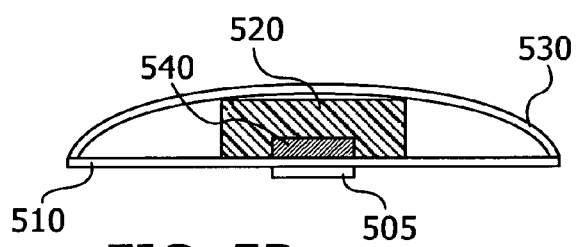
FIG. 5A
FIG. 5B
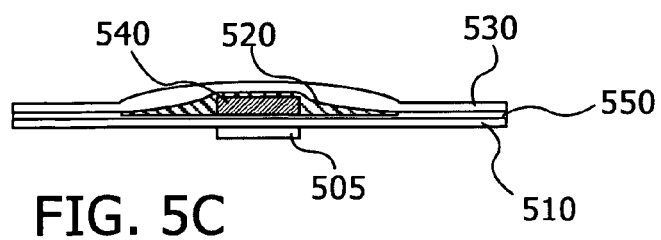
FIG. 5C

DISPOSABLE DIAPER WITH INTEGRAL DISPOSAL SYSTEM

CROSS-REFERENCE TO RELATED APPLICATIONS

The current application is a U.S. National Phase Application under 35 U.S.C. 371 of PCT International Application No. PCT/IL2010/000198, which has an international filing date of Mar. 10, 2010, and which claims the benefit of priority from Israel Patent Application No. 197,570, filed on Mar. 12, 2009, the disclosures of which applications are incorporated herein by reference.

FIELD OF THE INVENTION

The present invention relates generally to diapers and methods for their manufacture, and more specifically to diapers with integral disposal systems and methods for their manufacture.

BACKGROUND OF THE INVENTION

Over the last four decades, many improvements have been made in the development of disposable diapers. The diapers' appearance, absorbency, fit, softness, size and shaping have all been improved in many different ways.

However, diaper disposal still remains a problem with respect to hygiene, smell and disposal. Some efforts towards improving diaper disposal appear in the patent literature.

U.S. Pat. No. 4,034,760 discloses a combined disposable diaper and disposal bag wherein a thin plastic sheet is affixed over the waterproof side of a conventional disposable diaper and sealed to it along a portion of its periphery to form a permanently attached waterproof pocket with part of the sheet that can be turned inside out to form a bag for the used disposable diaper and to form a flap with the remainder of the sheet which can be closed over the bag opening to seal the bag.

U.S. Pat. No. 4,604,096 discloses a diaper assembly with integral disposal system, including a disposable diaper and an envelope integrally carried on the outside of the diaper, that has a mouth for receiving the diaper when soiled. One or more elements engage a section of the diaper with another section of the diaper to secure it on a wearer in a use configuration and restrict the mouth of the envelope in a disposal configuration.

U.S. Pat. No. 4,706,845 describes a unit combining a diaper dispenser and disposal drawer. The unit consists of two sections, an upper dispensing section and a lower disposal section, which provide a single unit for new and soiled diapers, as well as other supplies used in changing a baby. The upper dispensing section has a number of dividers which define vertical shafts. Diapers are placed in these shafts and are removable at the bottom thereof through adjustable slots. The slots of the upper dispensing section are adjustable by using a removable shelf. The vertical shafts are also adjustable in cross-sectional size to accommodate different sized diapers. A slidable front panel permits easy access to one or more of the vertical shafts for reloading. The bottom disposal section comprises a cabinet generally rectangular in shape with a pivoting, top-opening door. This disposal section may contain a separate bin, such as a plastic bag or bucket which is easily removed to dispose of soiled diapers and other waste. The door additionally has a liner along its edges making the lower section of the unit airtight and thus odor-free. Space is also provided to allow the user to place a deodorizer within the lower section.

FR2699401A1 describes a nappy (diaper) having a pouch built into its outer surface, containing a plastic bag which can be withdrawn through a hole in the outer wall of the pouch by pulling on a projecting tab. Once the bag has been withdrawn it can be turned inside out, enclosing the used nappy, pulling its top closed with a draw-string. The nappy can then be disposed of hygienically.

US2002029546 discloses a method for disposing of a soiled disposable diaper comprising the steps of: providing a bag made of a plastic material, the bag having a front panel and back panel integrally sealed together along the left and right side edges and the bottom side edge thereof and having an opening at a top edge of one of the panels, a seal flap connected to and being integral with a top edge of the other one of the panels, a strip of adhesive extending across the sealing flap and a cover strip extending across the front of the seal flap over the strip of adhesive, removing the cover strip, placing a soiled diaper in the plastic bag, folding the seal flap over the opening in the bag and onto an adjacent panel, pressing the strip of adhesive against the adjacent panel to generally seal the bag, and placing the generally sealed bag in a waste disposal container.

US2004176735 describes a packaged diaper, including a diaper, having a first, a nominal size, and a second, reduced size, the reduced size of the diaper being convenient for carriage and storage of the diaper. The diaper is disposed in an encasement in the second, reduced size. The encasement confines the diaper so that the diaper is retained in its reduced size by the encasement and so that the diaper is returned to its nominal size upon opening of the encasement.

EP0888766A describes a disposable nappy having a body, an outer surface of the body, and a pocket formed on the outer surface of the nappy for containing the body of the nappy when the used nappy is folded and the pocket is inverted neatly and easily, prior to disposal.

GB2414676A describes a disposable nappy which has a nappy sack incorporated into the back of the nappy. Preferably the nappy sack is released by pulling a tab which also forms the handle of the nappy sack. The nappy sack may envelop the nappy and be tied for hygienic disposal. This invention may eliminate the need for using separate nappy sacks.

FR2898488A describes an integrated device for wrapping used and rolled disposable nappy by a circular stretchable elastic fibrous membrane, which is integrated in the nappy in its external back and upper surface. The membrane comprises an orifice at the center of the membrane, which is provided with an elastic ring, and stretches when user grabs a central elastic ring.

WO0016679A describes a system for disposing of products of metabolism, especially human products of metabolism. The system consists of a base part which can be reused and a disposable multi-layer liner which is essentially adapted to fit the base part and is detachably fixed to the same. The invention also relates to a multi-layered, bag-shaped liner and to the use of this system and the liner in the fields of nursing, care of the elderly and care of infants.

DE102005007004A, to Gandolfo, describes a disposable nappy, which has a disposal bag stored between the inner absorbent layer and the impermeable outer layer. The disposal bag is permanently connected to the outer layer and can be pulled out from the inside of the nappy, via a slit-type opening to permit its disposal after use.

US2006282056, to Ramsey, describes one or more improvements includes a fluid-impermeable bag attached to or integral with a disposable diaper, the bag having closure elements on the outside of the front and back panels of the uninverted bag. After use, the bag is inverted over the soiled diaper and the closure elements interact, thereby closing and sealing the soiled diaper inside the bag. In some embodiments the bag is covered by a removable fabric element, such as a gauze panel, which may be decorated.

WO08023363 describes a bag attachable to an article to permit convenient disposal of the article after use, comprising a bottom section having an adherent outer surface for attachment to the article, a top section overlying the bottom section, and a tubular main section joined at one end to the bottom section, the tubular main section being of an expansible construction, normally in a contracted condition between the top and bottom sections, but being expandable to an expanded condition to define a compartment for receiving the article after use, at least one of the sections being formed with an opening to be used when introducing the used article into the compartment formed by the tubular main section in its expanded condition.

Despite the teachings of the publications hereinabove, there are no products available on the market, which address all the problems of diaper disposal. Moreover, the inventions described hereinabove do not provide full solutions to the aforementioned diaper disposal problems. For example, some of the aforementioned publications teach disposal bags placed within/adjacent to an absorbent layer of the diaper. This locally increases the thickness of the diaper. The disposal systems placed externally on an outer layer of the diaper interfere with the movement of a person wearing the diaper. As can be seen from FIG. 2 of US2006282056, the bag is attached to an impervious backing sheet, and requires the formation of an extra layer (cover 118) to cover the bag, which may be opened or dislodged by the movement of the person wearing the diaper. There therefore remains a need to provide ergonomic products for convenient and hygienic diaper and sanitary towel disposal.

SUMMARY OF THE INVENTION

It is an object of some aspects of the present invention to provide products and methods for diaper disposal.

In preferred embodiments of the present invention, improved methods and products are provided for disposing of diapers including:
  a) improving hygienic diaper disposal;
  b) improving comfort for diaper wearing relative to the products described hereinabove;
  c) improving ease of diaper disposal using one hand;
  d) reducing contact with soiled side of the diaper;
  e) providing a disposal bag which is not on an outer side of the diaper and therefore does not interfere with the baby/infant's clothing; and
  f) providing a disposal bag which is not on an outer side of the diaper and therefore does not interfere with the baby/infant's mobility.

There is thus provided according to some embodiments of the present invention, a diaper assembly with integral disposal system, comprising;
  a. a disposable diaper comprising;
    i. an outer layer comprising an aperture on an outer surface thereof;
    ii. an inner layer; and
    iii. an absorbent layer disposed between the outer layer and the inner layer;
  b. a bag disposed between the outer layer and the inner layer, the bag adapted to be retrieved via the aperture and to receive and enclose the diaper.

According to some embodiments, the outer layer includes a rear end section comprising a left re-sealable fastening tab and a right re-sealable fastening tab.

Further, according to some additional embodiments of the present invention, the outer layer includes a front end adapted to receive the left and right fastening tabs.

Additionally, according to some additional embodiments of the present invention, the rear end section includes a centrally disposed elasticated region between the left and right fastening tabs.

Yet further, according to some additional embodiments of the present invention, the bag is disposed in between the rear end of the outer layer and a posterior end of the absorbent layer.

According to some embodiments of the present invention, the bag is disposed in between the elasticated region and a posterior end of the absorbent layer.

In some cases, the aperture is disposed above the bag.

According to some additional embodiments of the present invention, the aperture is disposed parallel to and below the elasticated region.

In some cases, the aperture is one to five centimeters in length.

According to some additional embodiments of the present invention, the aperture includes a plurality of perforations.

Additionally, according to some embodiments of the present invention, the bag includes a wide-ended opening.

According to some additional embodiments of the present invention, a sealable tab is disposed on the wide-ended opening. Preferably, the tab is adapted to at least partially protrude through the aperture.

According to some additional embodiments of the present invention, there is a sticker disposed on the wide-ended opening. Preferably, the sticker is adapted to at least partially protrude through the aperture.

According to some additional embodiments of the present invention, the bag is of sufficient size to accommodate the diaper in a disposal configuration and the mouth of the envelope being sufficiently large to accept the diaper when the diaper is introduced into the bag.

According to some additional embodiments of the present invention, the bag includes adhesive means disposed proximal to the wide-ended opening for sealing the bag after introduction of the diaper into the bag. The adhesive means is adapted to seal the bag so as to reduce odors from the diaper, Additionally, according to some additional embodiments of the present invention, wherein the bag is folded along a horizontal axis and a vertical axis. Preferably, the bag is folded under pressure.

According to some additional embodiments of the present invention, the absorbent layer is of a greater thickness than the height of the folded bag.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a simplified exploded diagram of a diaper with an integrated disposal system, in accordance with an embodiment of the present invention;

FIG. 1B is a simplified diagram of an external view of an outer layer of a diaper with an integrated disposal system, in accordance with an embodiment of the present invention;

FIGS. 2A-2D are simplified pictorial illustrations of disposal bags of the integrated disposal systems of FIG. 1A, in accordance with some embodiments of the present invention;

FIG. 3A is a simplified pictorial illustration of a disposal bag aperture on an outer surface of a diaper of with the integrated disposal system of FIG. 1A, in accordance with an embodiment of the present invention;

FIG. 3B is a simplified pictorial illustration of folding the disposal bag of FIG. 2A, in accordance with an embodiment of the present invention;

FIG. 3C is a simplified pictorial illustration of another disposal bag aperture on an outer surface of a diaper of with the integrated disposal system of FIG. 1A, in accordance with an embodiment of the present invention;

FIG. 3D is a simplified pictorial illustration of another disposal bag aperture on an outer surface of a diaper of with the integrated disposal system of FIG. 1A, in accordance with an embodiment of the present invention;

FIG. 4 is a simplified pictorial illustration of an end view from a rear edge of a diaper with an integrated disposal system, in accordance with an embodiment of the present invention;

FIG. 5A is a simplified exploded diagram of a sanitary towel with an integrated disposal system, in accordance with an embodiment of the present invention;

Figure 1A:
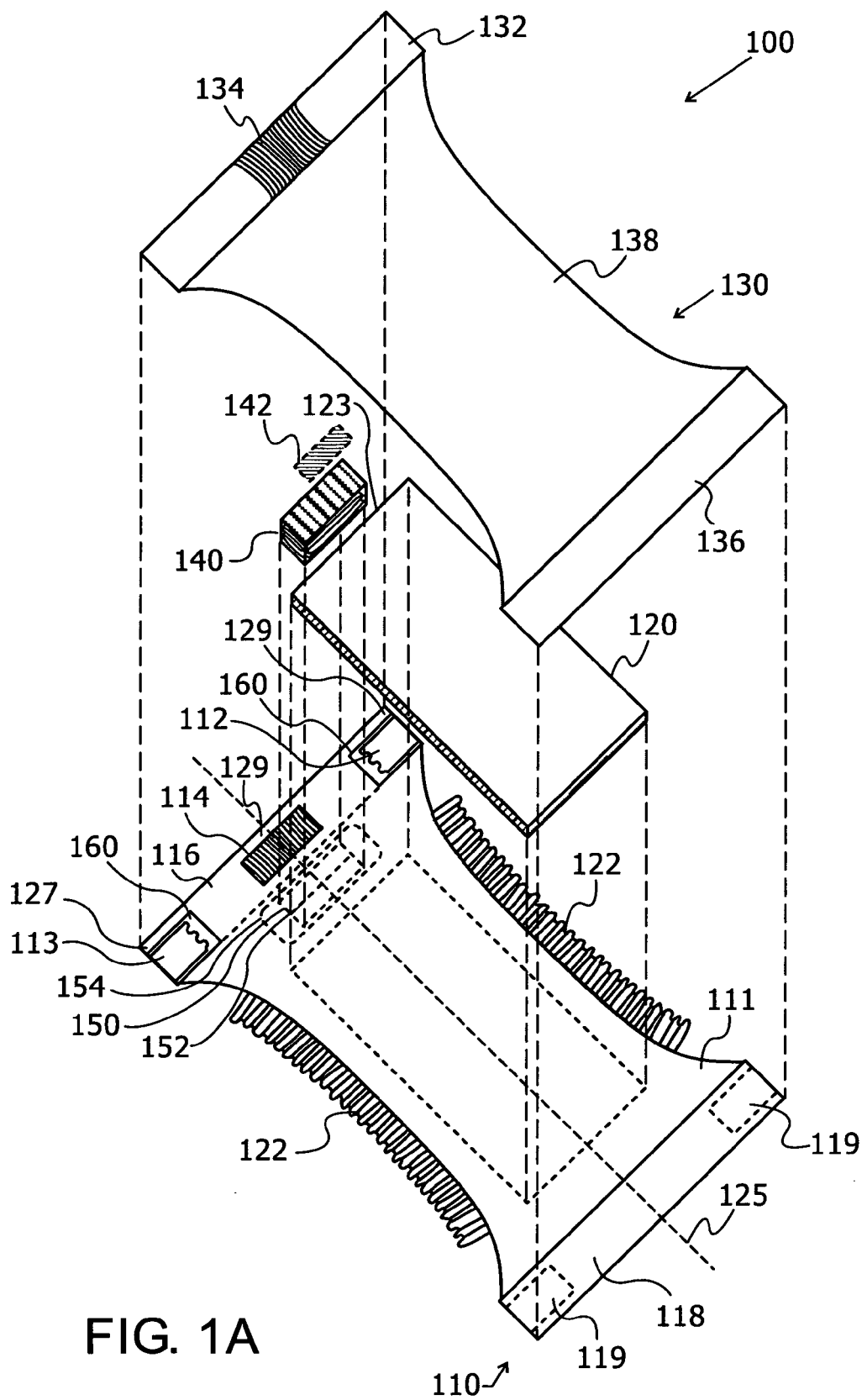

FIG. 5B is a simplified pictorial illustration of an end view from a rear end of a sanitary towel with an integrated disposal system, before bonding, in accordance with an embodiment of the present invention; and FIG. 5C is a simplified pictorial illustration of an end view from a rear end of a sanitary towel with an integrated disposal system, after bonding, in accordance with an embodiment of the present invention.

In all the figures similar reference numerals identify similar parts.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

In the context of this invention, the word "diaper" or "sanitary product" is meant to broadly include, but not be limited to all available brands and types of disposable and non-disposable baby diapers, baby nappies, infant diapers, infant disposable panties, adult incontinence diapers, sanitary towels, adult incontinence panties and diapers for pets and animals.

The diapers of the present invention may be made of any suitable materials, used in the diaper industry and known in the art.

To date, most parents, nurses and assistants (termed herein "care providers") suffer from the direct odors emanating from diapers or indirectly from diaper bins or pails. Additionally, upon changing the diaper of a baby or adult, the care providers often get their hands or arms soiled from excreta and/or urine. Despite the availability of diaper sacks and bags sold separately, these do not sufficiently reduce the odors or contact of the care providers with the excreta and/or urine.

The current invention provides diapers with in-built disposal systems, designed to minimize odors and bodily contact with excreta. Reference is now made to FIG. 1A, which is a simplified exploded diagram of a diaper 100 with an integrated disposal system, in accordance with an embodiment of the present invention.

Diaper 100 comprises a lower outer layer 110, an inner layer 130 and an absorbent thick middle layer 120. The absorbent layer typically extends 60-80% of the length of the outer layer and 70-90% of the narrowest width of the outer layer.

Lower outer layer 110 may be waterproof or water resistant, thereby ensuring that wetness from excretions remains within the diaper and does not wet the clothing of the wearer. Lower outer layer 110 comprises a rear end section 116 and a front end section 118. Most diapers are symmetrical about a longitudinal axis 125 extending down the length of the diaper. Most modern diaper designs include on the rear end section a couple of fastening tabs (see US2004087929A, as a non-limiting example). Diaper 100 comprises left and right re-sealable fastening tabs, 112, 113, disposed around a left edge 129 and a right edge 127 respectively of the rear end section, as is known in the art. The left and right re-sealable fastening tabs, 112, 113, are received by two receiving portions 160, which allow the tabs to be sealed, removed and adjusted, as is known in the art.

Rear end section 116 typically comprises a centrally disposed elasticated region 114 disposed centrally and symmetrically about axis 125. It should be understood that in some designs, the elasticated region may comprise elastic and in others, the material may be folded in a way to effect a stretchable property. Many variations on these designs are known in the art.

Lower outer layer 110 also comprises a pair of longitudinal tethered leg flaps 122 adapted to provide close fit around the legs of the wearer. These flaps may comprise elasticated material, gathered material or any other suitable design to prevent leakage from the diaper to the legs, as is known in the art.

The absorbent thick middle layer 120 is typically glued/affixed to an inner side 111 of the lower outer layer 110, in between the rear end section 116 and the front end section 118 as is seen in FIG. 1A.

Inner layer 130 is adapted to contact and cover the genitals, anal region and, at least partially, the buttocks of the wearer, so as to receive urine and faeces excreted by the wearer. Inner layer 130 is typically glued/affixed onto the absorbent layer and onto the lower outer layer around the absorbent thick middle layer, as is known in the art. Inner layer 130 comprises a rear end 132 and a front end 136. The rear end 132 may also comprise an elasticated region 134. The shape of the inner layer typically is identical or similar to that of the lower outer layer.

Figure 4:
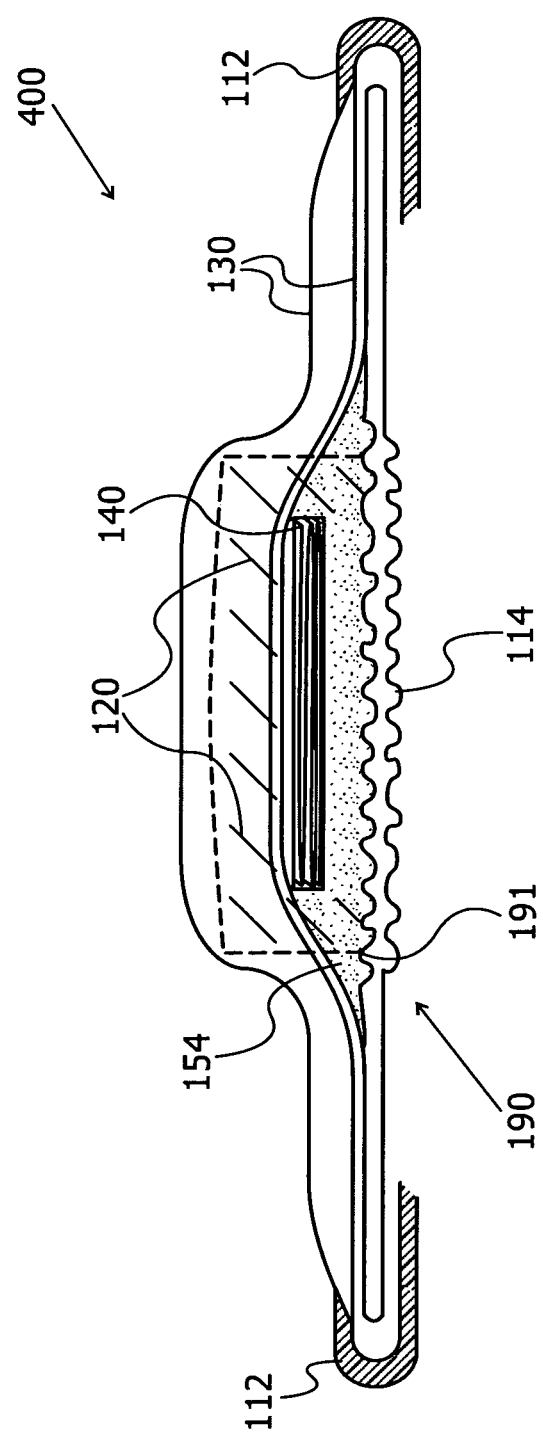

The present invention provides diaper 100 with an integrated disposal system 190 (see also FIG. 4).

Integrated disposal system 190 comprises an access region 150 with an aperture 152 on lower outer layer 110. Integrated disposal system 190 is disposed symmetrically about axis 125. Integrated disposal system 190 comprises a disposal bag 140, which is folded and disposed in between inner layer 130 and lower outer layer 110. The bag is conveniently housed in an air pocket 154 in between rear end section 116 a rear edge 123 of the absorbent thick middle layer 120.

According to some embodiments, the bag may fully removed from the diaper via the aperture. According to other embodiments, the bag may optionally be glued with adhesive 142 to the inner layer, and thus may only be partially removed from the diaper.

Figure 2A:
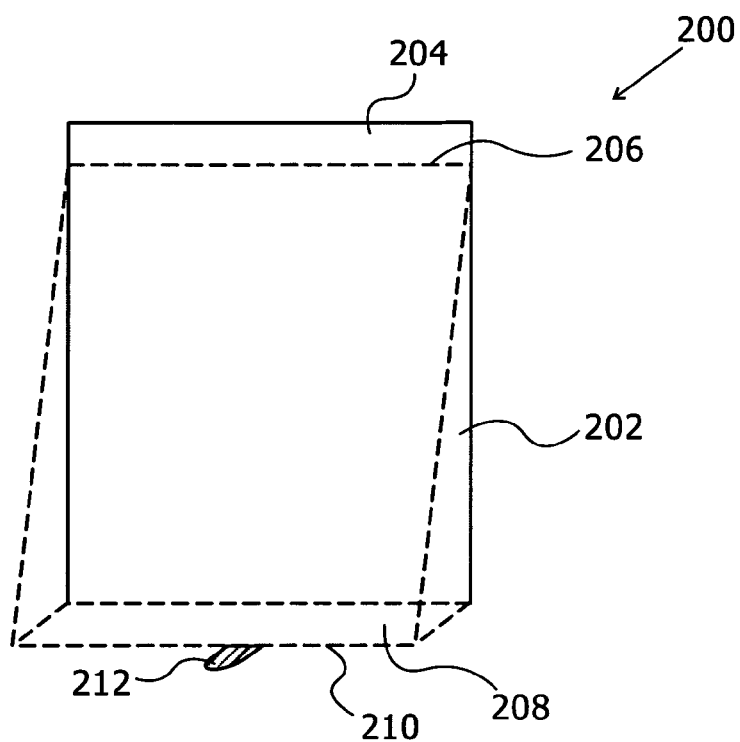
Figure 2B:
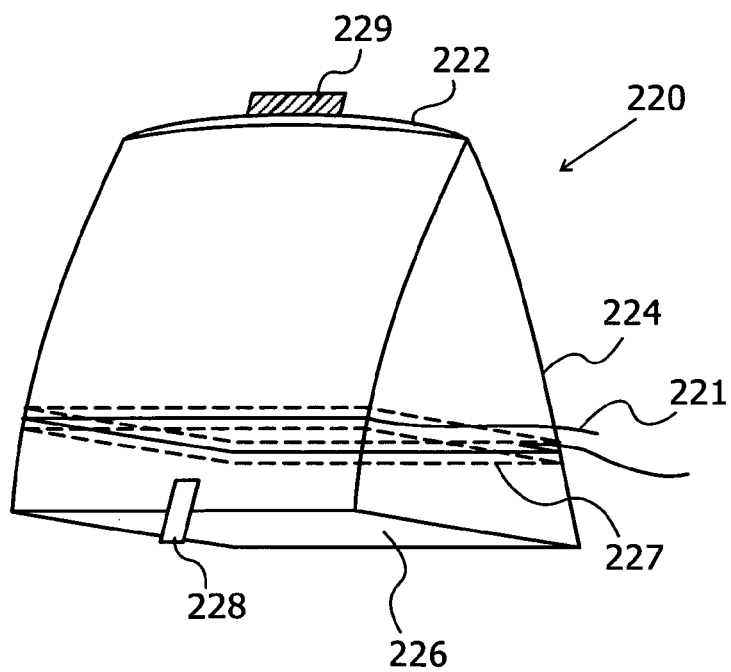

According to some further embodiments, the bag may comprise an additional tab 229 for sticking to the inner layer 130 on the sealed end 222 (FIG. 2B). The sealed end may be straight (as shown in the FIG. 2A or curved as shown in FIG. 2B. The additional tab may be narrow or may preferably be of a similar width to aperture 152.

When the bag is retrieved via aperture 152, it remains stuck at the sealed end to the inner layer. The carer places his/her hand within the bag and turns it inside out, thereby wrapping around the soiled diaper. The bag is closed by means of the tab 212 or sealing element 245, 247, for example.

As can be seen in FIG. 2B, the bag may also contain a thread 221 housed in a thread holder 227 which is disposed at a distance away from the opening 226. This thread can be used to tie the bag after the soiled nappy has been placed therein (in addition to the tab/sticker or sealing elements as described herein).

Figure 1B:
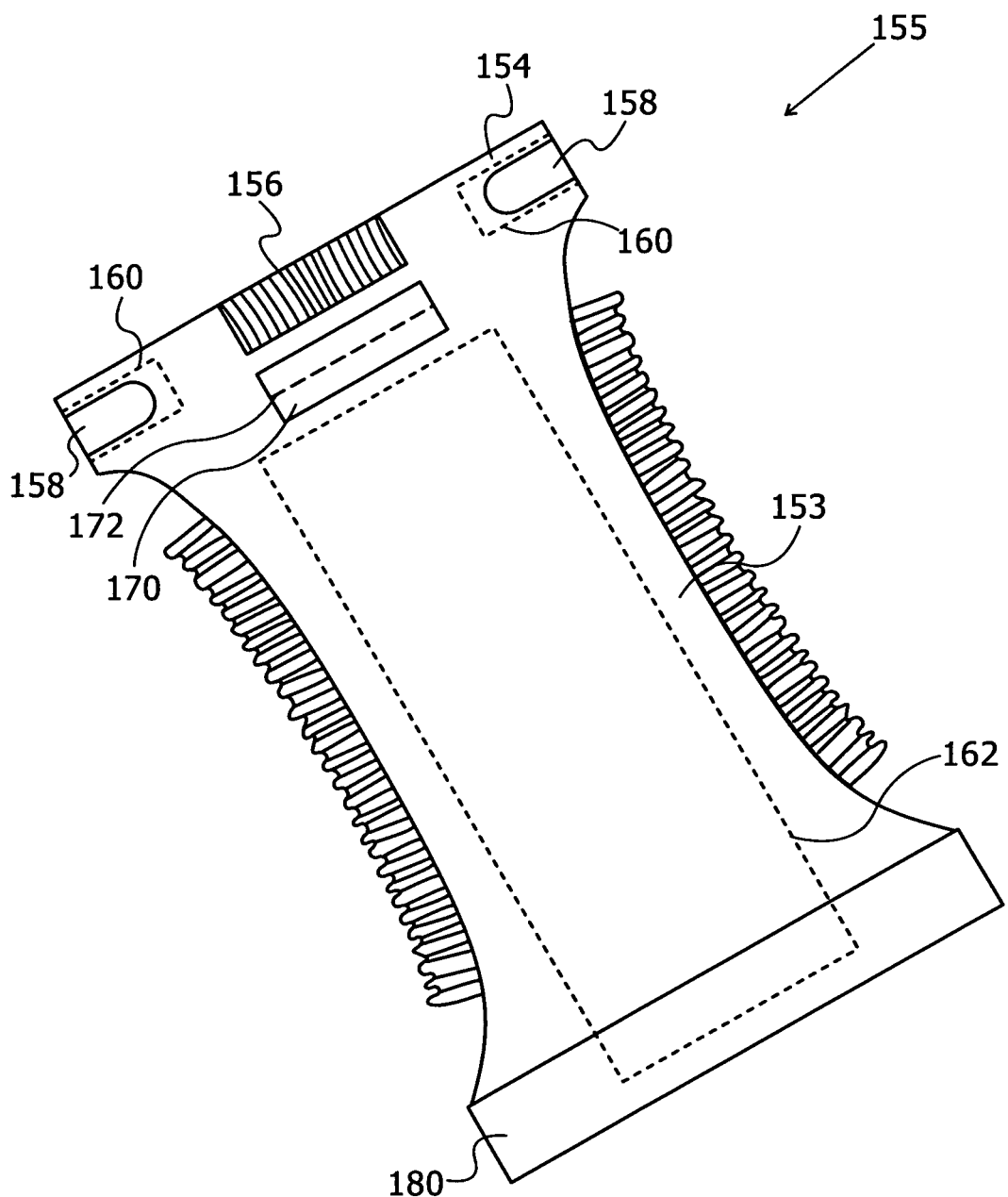

Reference is now made to FIG. 1B, which is a simplified diagram of an external view 155 of lower outer layer 110 of diaper 100 with an integrated disposal system, in accordance with an embodiment of the present invention.

The lower outer layer has an external side 153. A bulge 162 is seen from the absorbent thick middle layer 120. Rear ends 158 of re-sealable fastening tabs, 112, 113 are seen along the rear end section. In between an outer elasticated region 156 of rear end section 116 and bulge 162, there is seen an outer face 170 of the access region and aperture 172 (similar or identical to aperture 152, FIG. 1A).

Turning now to FIGS. 2A-2D, there can be seen simplified pictorial illustrations of disposal bags 200, 220, 230 and 240 of the integrated disposal systems 190, in accordance with some embodiments of the present invention.

Bag 200 comprises a sealed end 204 having a seal line 206 and at an opposing open end 210, an opening 208 and a sealable tab 212 affixed to or integrally formed with the open end. Bag 200 may be made of any suitable polymer known in the art. According to some embodiments, bag 200 is made of a biodegradable polymer, known in the art.

Another type of bag (or sack) is a wide-opened bag 220 having a sealed end 222, and a wide opening 226 for received the soiled diaper.

Additionally, according to some embodiments, bag 200 may comprise a zipper-like vacuum seal (not shown) as is known in the art for freezer bags and vegetable bags.

According to some embodiments, a bag 230 may comprise a long side 238 and a short side 236. This type of bag is suitable for sealing with a sealing tab 239 on an outer edge 237 of the long side, which may conveniently be wrapped over the short side and stuck thereupon.

According to some further embodiments, an envelope-type bag 240 may be used. Envelope-type bag 240 comprises one sealed end 242 and an opposing open end 244. Bag 240 comprises a long rear side 248 with a long sealing element 245 disposed proximal to an open end 247 thereof and a shorter front side 246 comprising a second long sealing element 243 disposed proximally to the open end 244. In some cases, the second long sealing element 243 may be disposed proximal to the sealed end (not shown), to reduce odors. In some further cases, a second long sealing element 243 may disposed on an inner side of the front side (not shown). Many variations on the number and positions of the sealing elements and tabs are deemed to be within the scope of the present invention.

Though not shown in the figures, it should be understood that the present invention encompasses bags which contain more than one tab, sealable element, vacuum seal and thread. Various combinations may be used seal the bag in order to minimize or eliminate odors from the soiled diaper.

Figure 3A:
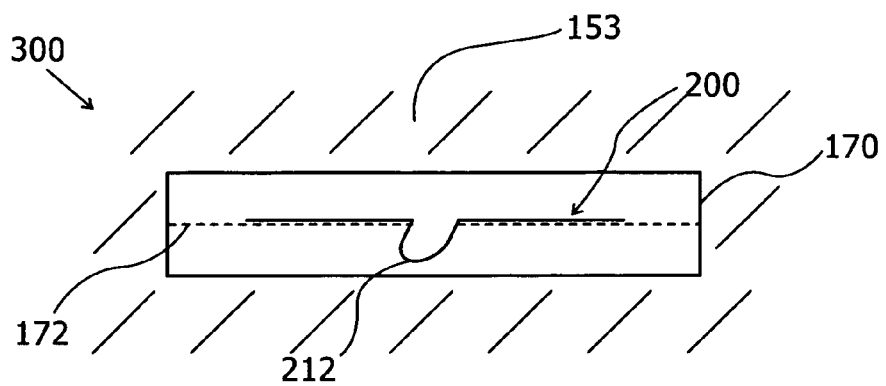

Reference is now made to FIG. 3A, which is a simplified pictorial illustration of an external view of disposal bag aperture 300 on an external side 153 of diaper 100 of with integrated disposal system 190, in accordance with an embodiment of the present invention.

External side 153 of lower outer layer 110 comprises the outer face of the access region 170 and aperture 172 of the integrated disposal system 190. Sealable tab 212 protrudes outwardly from the aperture for convenient pulling of the bag from out of air pocket 154 to wholly or partially remove the bag from the interior of the diaper. The sealable tab may be stuck onto the diaper with a re-sealable glue or with other means, such as Velcro.

It should be understood that the bags may be of the form of any disposable bag known in the art and that the illustrated examples should not be deemed limiting. Some disposable bags have little handles at the open end for example. Others have a seam at the closed end and a vertical seam along one length of the bag.

Figure 3B:
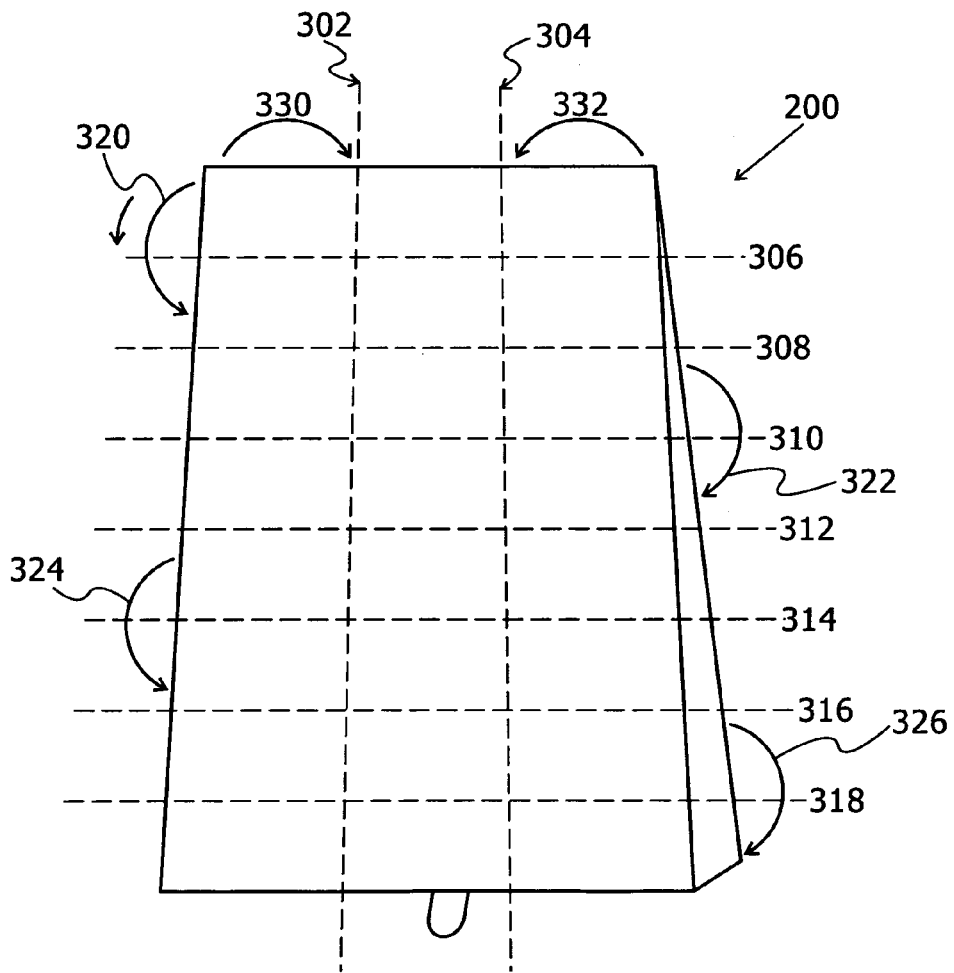

Reference is now made to FIG. 3B, which is a simplified pictorial illustration of folding a disposal bag, in accordance with an embodiment of the present invention.

A bag, such as disposal bags 200, 220, 230 and 240, may be folded along one or more vertical axes 302, 304, and further along one or more horizontal axes 306, 308, 310, 312, 314, 316 and 318. Typically, the bag is 20-30 cm in length and 10-30 cm in width. According to some embodiments, the bag may be folded to a harmonica form (in the directions of arrows 320, 322, 324 and 326). According to other embodiments, the bag may be wrapped around itself.

Figure 2C:
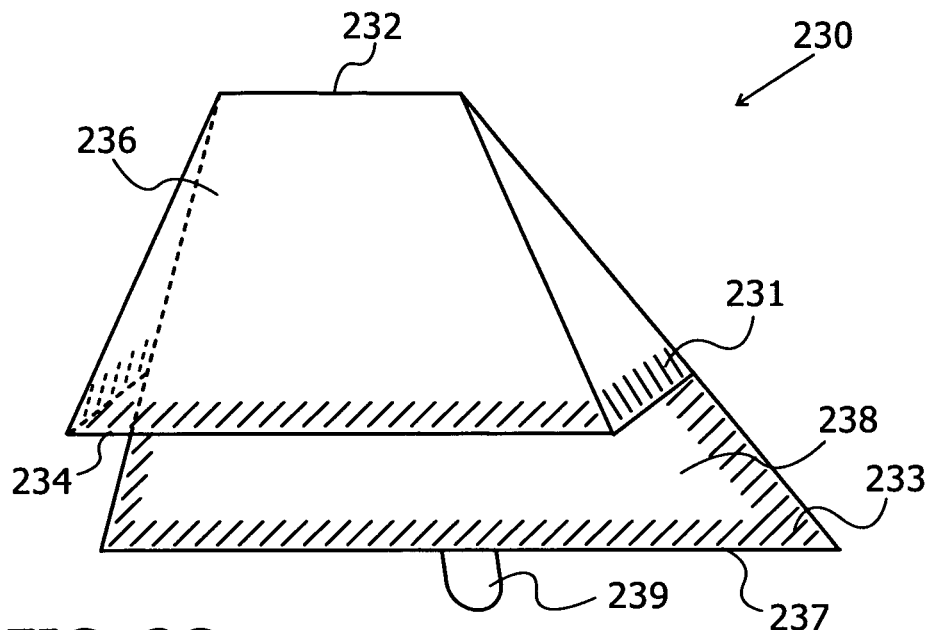
Figure 2D:
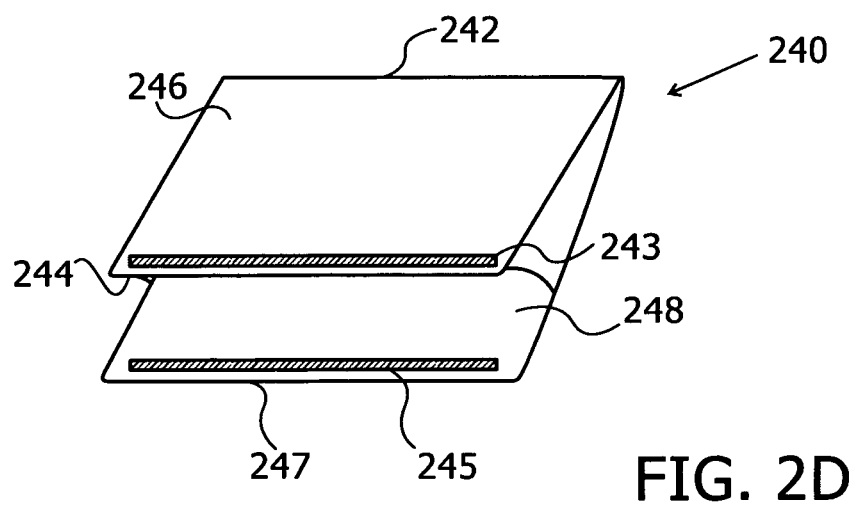

As can be seen in FIG. 2C, the bag comprises sealing elements 231 and 233 which are disposed around sides of outer edge 237 and inner edge 234 edges of the long side 238 and the short side 236 of the bag respectively. It should further be understood that there may be such sealing elements in all the bags described herein (though not shown, for the sake of simplicity). One main embodiment of the current invention is to enable hermetic closure of the bags to prevent or reduce the odors from the soiled diaper, when placed in the bag.

The folded bag typically is of a rectangular cross section of a smaller dimension than that of the access region 150. The access region may be of around 2-8 cm in width and 0.3 to 3 cm in height. Thus the folded bag will typically be of minimal height of 0.1-0.3 cm and of 2-6 cm in width and 0.3 to 2 cm in height.

Figure 3C:
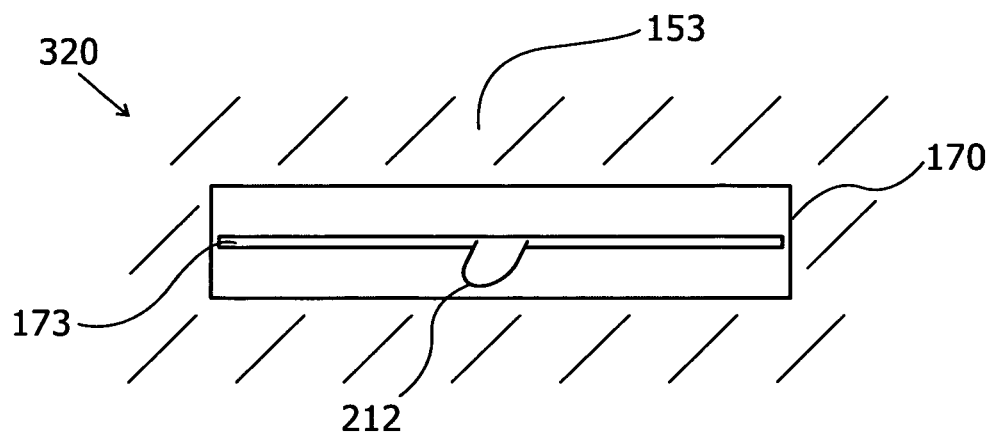

Reference is now made to FIG. 3C, which is a simplified pictorial illustration of another an external view 320 of a disposal bag aperture 173 on an outer surface 153 of diaper 100 of with the integrated disposal system 190, in accordance with an embodiment of the present invention.

Aperture 173 is in the form of a slit, which extends for all or most of the length of access region 170. Part of the sealable tab 212 (or tongue) is seen to pass through slit 173. The tab or tongue may be disposed across part or all of the slit and may be of any suitable width. The tab may be an integral part of side 208 or may be distinct therefrom. The bag is fixed (and may also be glued) within air pocket 154 and cannot be released by itself through the slit without pulling on tab 212.

Figure 3D:
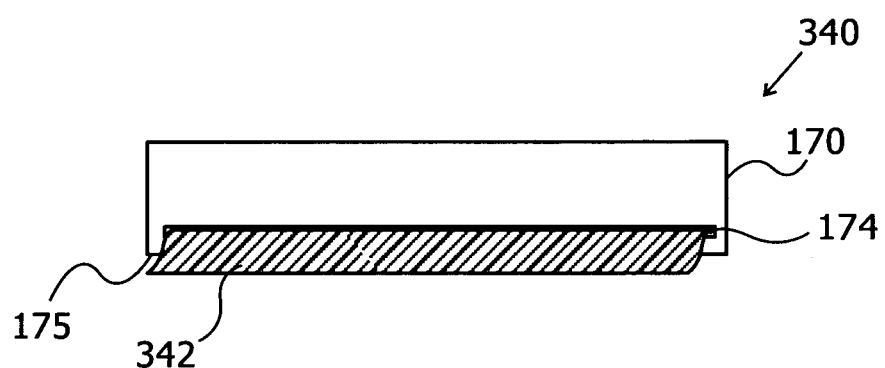

Reference is now made to FIG. 3D, which is a simplified pictorial illustration of another disposal bag aperture 340 on an outer surface of a diaper 100 of with the integrated disposal system 190, in accordance with an embodiment of the present invention.

As can be seen in FIG. 3D, an aperture 174 is disposed horizontally in the form of a slit towards a lower edge 175 thereof, which extends for all or most of the length of access region 170. The aperture may be disposed at any height of the access region. The example shown in FIG. 3D should not be deemed as limiting.

Reference is now made to FIG. 4, which is a simplified pictorial illustration of an end view 400 from a rear edge 129 (FIG. 1A) of diaper 100 with an integrated disposal system 190, in accordance with an embodiment of the present invention.

As can be seen in FIG. 4, the absorbent thick middle layer 120 forms the bulk of the thickness of the diaper, being disposed between the lower outer layer and inner layer 130. Disposal bag 140 sits within air pocket 154 in between the elasticated region 114 and the absorbent thick middle layer 120. The disposable bag may also be protected and held in place by a retaining element 191. Retaining element is typically a thin layer of material which is bonded to the lower outer layer 110.

As can be seen from the description herein, the diaper disposal systems of the present invention do not interfere with the advantages of the appearance and/or production of diapers known in the art. Furthermore the production steps of the three layers, namely:

i. the outer layer comprising an aperture on an outer surface thereof;
ii. the inner layer; and
iii. the absorbent layer disposed between the outer layer and the inner layer.

The bag does not bulge out beyond the thickness of the absorbent thick middle layer 120 and thus does not interfere with mobility or comfort of the wearer, nor with the clothing of the wearer. Prior art publication U.S. Pat. No. 4,604,096, FR2699401A1, GB2414676A, DE102005007004A and WO08023363 described hereinabove all teach systems with disposal devices on an outer side of the diaper, which interfere with clothing, comfort and mobility of the wearer. US2006282056 teaches a system in which an extra cover is bonded onto the backing layer and the bag is disposed between the cover and backing layer.

Reference is now made to FIG. 5A, which is a simplified exploded diagram of a sanitary towel 500 with an integrated disposal system 590 (FIG. 5B). Sanitary towel 500 comprises a lower backing impervious layer 510, an intermediate absorbent layer 520 and an upper layer 530. The absorbent layer has a smaller footprint than the upper and lower layers leaving an unpadded perimeter 511 surrounding the padded layer. Sanitary towel 500 has a front end 512 and a rear end 514. Sanitary towel 500 comprises one or more adhesive strips 505 disposed a length of the lower backing impervious layer 510. Integrated disposal system 590 is disposed on the unpadded perimeter between the absorbent layer and the rear end. Integrated disposal system 590 comprises a folded disposal bag 540 disposed in an air pocket 554 on an access region 550 with an aperture 552 on lower layer 510.

As can be seen in FIG. 5B, the integrated disposal system 590 is of a height less than that of the absorbent layer. FIG. 5C is a simplified pictorial illustration of an end view from a rear end of a sanitary towel with an integrated disposal system, after bonding of the upper layer to the lower layer and at least partial removal of the air pocket. It should be understood that the teachings of the integrated disposal system 590 of sanitary towel 500 (FIGS. 5A-5C) may be applied to almost any standardized commercially produced sanitary towel, such as a sanitary towel with flaps, a thin towel and the like.

The advantages of the integrated disposal systems of the present invention include:

no requirement for an additional layer beyond the lower layer
does not bulge out beyond the height of the absorbent layer
does not touch on the absorbent layer and is thus hygienic
easy to manufacture
easy to remove bag from access area via slit
low production costs
does not interfere with outer appearance of the sanitary product or diaper
compact
may be made of a biodegradable material
enables easy and hygienic disposal of soiled or wet sanitary products Additionally or alternatively, an integrated disposal system may be constructed and configured on an adult incontinence pad. The examples shown herein are exemplary and should not be deemed limiting.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A diaper assembly with an integral disposal system, comprising:
   a. a disposable diaper comprising:
      i. an outer layer comprising an aperture on an outer surface thereof and a rear end section;
      ii. an inner layer; and
      iii. an absorbent layer disposed between said outer layer and said inner layer, said absorbent layer having a rear edge; and
   b. an integral disposal system comprising:
      i. a bag disposed in an air pocket between said outer layer and said inner layer, said air pocket disposed without contact with said absorbent layer, said bag adapted to be retrieved via attached sealable tab protruding outwards from the aperture in said outer layer and to receive and seal said diaper with said tab;
   wherein said absorbent layer is of a greater thickness than a height of said air pocket; wherein the aperture comprises a plurality of perforations.

2. The diaper assembly of claim 1, wherein said rear end section comprises a left resealable fastening tab and a right re-sealable fastening tab.

3. The diaper assembly of claim 2, wherein the rear end section comprises a centrally disposed elasticated region between said left and right fastening tabs.

4. The diaper assembly of claim 3, wherein the air pocket is disposed in between the elasticated region and said rear edge of said absorbent layer.

5. The diaper assembly of claim 4, wherein the aperture is disposed above said air pocket.

6. The diaper assembly of claim 5, wherein the aperture is disposed parallel to and below said elasticated region.

7. The diaper assembly of claim 1, wherein said bag is biodegradable.

8. The diaper assembly of claim 7, wherein said disposable diaper is biodegradable.

9. The diaper assembly of claim 1, wherein the bag is adapted to be fully removed from said diaper assembly.

10. The diaper assembly of claim 1, wherein the bag is at least partially connected to said inner layer, thereby being adapted to be partially removed from said diaper assembly.

11. The diaper assembly of claim 1, wherein the bag comprises a sealable tab.

12. The diaper assembly of claim 11, wherein said tab is adapted to attached to said inner layer.

13. The diaper assembly of claim 1, wherein said bag is adapted to receive the disposal diaper and to enable hermetic closure therearound.

14. The diaper assembly of claim 13, wherein said disposable diaper is soiled, and said closure is adapted to substantially reduce odors from said soiled diaper.

15. The diaper assembly of claim 1, wherein the bag comprises a wide-ended opening.

16. The diaper assembly of claim 15, comprising a tab disposed on said wide-ended opening.

17. The diaper assembly of claim 16, wherein said tab is adapted to at least partially protrude through said aperture.

18. The diaper assembly of claim 17, wherein said bag is of sufficient size to accommodate said diaper in a disposal configuration and the mouth of said bag is sufficiently large to accept said diaper when said diaper is introduced into said bag.

19. The diaper assembly of claim 18, wherein said bag comprises adhesive means disposed proximal to said wide-ended opening for sealing said bag after introduction of the diaper into the bag.

* * * * *